US00PP19259P2

(12) United States Plant Patent
Korlipara

(10) Patent No.: US PP19,259 P2
(45) Date of Patent: Sep. 23, 2008

(54) ***HAKONECHLOA MACRA* PLANT NAMED 'STRIPE IT RICH'**

(50) Latin Name: *Hakonechloa macra*
Varietal Denomination: Stripe it Rich

(75) Inventor: Harini Korlipara, Canby, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 0 days.

(21) Appl. No.: 11/904,678

(22) Filed: Sep. 27, 2007

(51) Int. Cl.
*A01H 5/00* (2006.01)

(52) U.S. Cl. ..... Plt./384

(58) Field of Classification Search ..... Plt./384
See application file for complete search history.

*Primary Examiner*—Annette H Para
*Assistant Examiner*—S. B. McCormick-Ewoldt
(74) *Attorney, Agent, or Firm*—Klarquist Sparkman, LLP

(57) ABSTRACT

A new and distinct *Hakonechloa* plant named 'Stripe it Rich' characterized by gold foliage variegated with white stripes and excellent vigor.

1 Drawing Sheet

Botanical denomination: *Hakonechloa macra.*
Variety designation: 'Stripe it Rich'.

BACKGROUND OF THE INVENTION

The present invention relates to a new and distinct cultivar of *Hakonechloa macra* given the cultivar name 'Stripe it Rich'. *Hakonechloa* is in the family *Poaceae.* This new cultivar originated as a tissue culture mutation from *Hakonechloa macra* 'All Gold', an unpatented plant.

SUMMARY OF THE INVENTION

This new *Hakonechloa* cultivar is unique by being the only variegated gold leaf form known to the breeder. It is characterized by:

1. Gold foliage variegated with white stripes; and
2. Excellent vigor.

This new cultivar has been reproduced only by asexual propagation (division and tissue culture). Each of the progeny exhibits identical characteristics to the original plant. Asexual propagation by division and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE PHOTOGRAPHS

FIG. 1 shows a one-year-old plant of *Hakonechloa macra* 'Stripe it Rich' growing in a one gallon pot in mid-summer in Canby, Oreg.

FIG. 2 shows the same plant after growing in full sun for two weeks.

DETAILED PLANT DESCRIPTION

The following is a detailed description of the new *Hakonechloa* cultivar based on observations of a one-year-old specimen growing in containers in a cool greenhouse in Canby; Oreg. Canby is in Zone 8 on the USDA Hardiness map. Temperatures range from a high of 95 degrees F. in August to an average of 32 degrees F. in January. Normal rainfall is 42.8 inches per year in the trial fields in Canby, Oreg. The color descriptions are all based on The Royal Horticultural Society Colour Chart.

Plant:
- *Type.*—Herbaceous perennial grass with slow creeping rhizomes which dies down to the ground in winter.
- *Hardiness.*—USDA Zones 6 to 9.
- *Size.*—Grows to 50 cm wide and 14 cm tall.
- *Form.*—Basal clump.
- *Vigor.*—Excellent.
- *Roots.*—Coarsely fibrous, ivory in color, Yellow White 158B, new plants grow easily from crown divisions.

Culms:
- *Type.*—Arching.
- *Size.*—Grows to 21 cm long and 2.5 mm wide.
- *Internode length.*—2 to 3 cm.
- *Surface texture.*—Sparsely pubescent.
- *Color.*—Yellow Green 146C.

Leaf:
- *Type.*—Simple.
- *Shape.*—Broadly linear.
- *Arrangement.*—Basal, stem leaves alternate.
- *Blade.*—Grows to 19 cm long and 5 to 11 mm wide.
- *Margins.*—Minutely scabrous, flat to loosely involute.
- *Apex.*—Acuminate.
- *Base.*—Clasping, collar pubescent.
- *Surface texture.*—Glabrous on both sides.
- *Venation.*—Parallel.
- *Color.*—Top bottom sides — Yellow Green 154A in spring to Yellow Green 144A late summer with the variegation White 155A. Sheath — Yellow Green 146C in shade and Greyed Orange 176B in sun. Collar — Yellow Green 146C in shade and Greyed Purple 187B in sun.
- *Inflorescence.*—Terminal open panicles, grows to 17 cm long and 12 cm wide, with the branches geminate, scabrous, spikelets Yellow Green 146C, linear-oblong, 1 to 2 cm long, glumes broadly lanceolate, acute, 3 to 4 mm and 4 to 5 mm long, respectively, lemmas broadly lanceolate, 6–7 mm long, the awn slender, erect, ½ to ⅘ as long as the lemma, rachilla joints about 2 mm long, with long white hairs, anthers 2 to 3 mm long, caryopsis about 2 mm long, glabrous with a shallow grove on the ventral side at the base.

*Bloom time.*—Late summer to early fall.

Seed:

*Description.*—Caryopsis about 2 mm long, glabrous with a shallow grove on the ventral side at the base.

*Fertility.*—Good.

Disease and pests: *Hakonechloa* get infrequent damage from diseases and pests. The new cultivar has no known resistances.

COMPARISONS TO SIMILAR *HAKONECHLOA*

Compared to *Hakonechloa macra* 'All Gold', the parent plant, the new cultivar is variegated.

Compared to *Hakonechloa macra* 'Aureola', an unpatented plant, the new cultivar has gold leaves with white variegation rather than green leaves with gold variegation.

I claim:

1. A new and distinct *Hakonechloa* plant as herein illustrated and described.

* * * * *

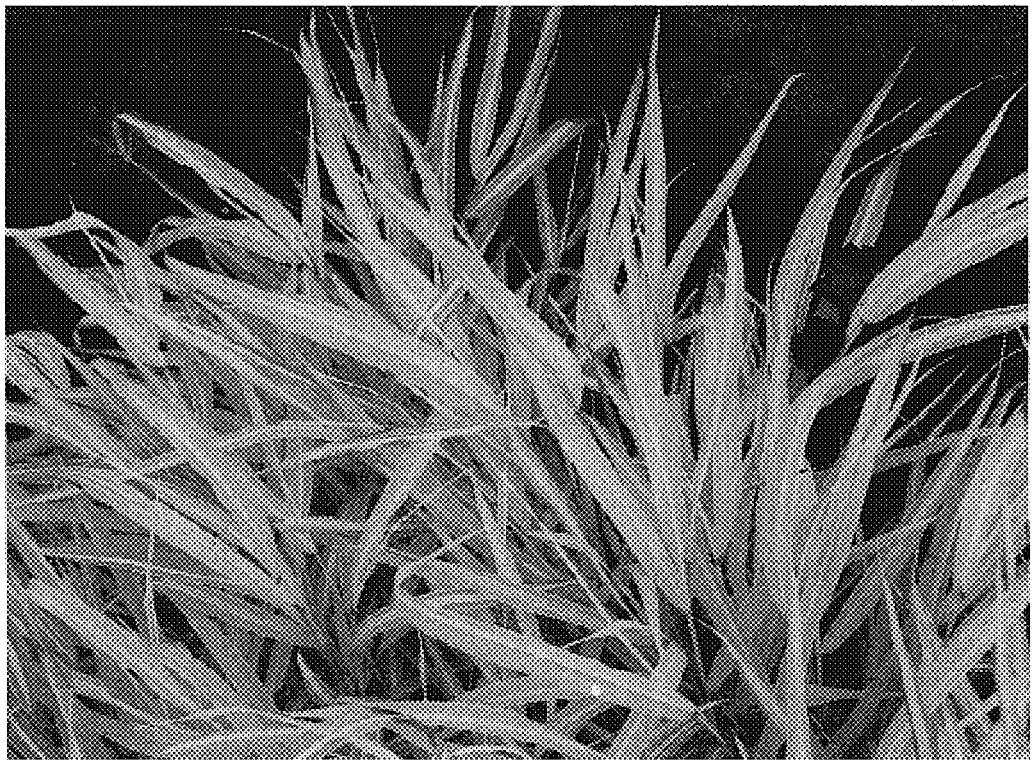

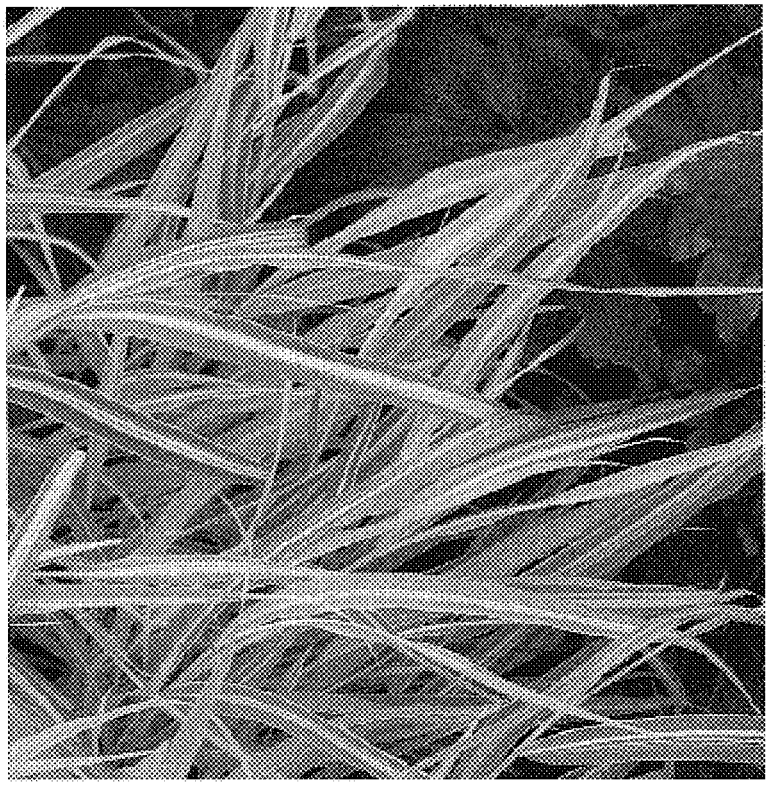
Figure 1 above, Figure 2 below.